United States Patent
Horiuchi et al.

(10) Patent No.: US 12,205,314 B2
(45) Date of Patent: *Jan. 21, 2025

(54) IMAGE PROCESSING APPARATUS FOR A PLURALITY OF TIMESERIES IMAGES ACQUIRED BY AN ENDOSCOPE, IMAGE PROCESSING METHOD, AND RECORDING MEDIUM

(71) Applicant: OLYMPUS MEDICAL SYSTEMS CORP., Tokyo (JP)

(72) Inventors: Kazuhito Horiuchi, Tokyo (JP); Takuya Matsunaga, Tokyo (JP); Takashi Miyoshi, Kanagawa (JP); Munenori Fukunishi, Tokyo (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 317 days.

This patent is subject to a terminal disclaimer.

(21) Appl. No.: 17/903,135

(22) Filed: Sep. 6, 2022

(65) Prior Publication Data
US 2024/0078694 A1 Mar. 7, 2024

(51) Int. Cl.
*G06T 7/60* (2017.01)
*G06T 7/571* (2017.01)
(Continued)

(52) U.S. Cl.
CPC .............. *G06T 7/60* (2013.01); *G06T 7/571* (2017.01); *G06T 17/00* (2013.01); *G06V 10/24* (2022.01);
(Continued)

(58) Field of Classification Search
None
See application file for complete search history.

(56) References Cited

U.S. PATENT DOCUMENTS 11,782,325 B1 * 10/2023 Miyoshi ................ H04N 23/67
2014/0176692 A1 6/2014 Tsuyuki et al.
(Continued)

FOREIGN PATENT DOCUMENTS

EP 2 868 254 A1 5/2015
EP 3 513 704 A1 7/2019
(Continued)

OTHER PUBLICATIONS

Tinghui Zhou, et al., "Unsupervised Learning of Depth and Ego-Motion from Video", 2017 IEEE on Computer Vision and Pattern Recognition(CVPR), Jul. 21-26, 2017, IEEE.

*Primary Examiner* — Tyler W. Sullivan
(74) *Attorney, Agent, or Firm* — Scully, Scott, Murphy & Presser, P.C.

(57) ABSTRACT

Provided is an image processing apparatus including a processor. The processor is configured to: reconstruct, by employing a plurality of time-series images acquired by an endoscope, three-dimensional information of an imaging subject containing relative dimensions; calculate, on the basis of focus information of each of the plurality of images, scale information for converting the relative dimensions of the three-dimensional information to absolute dimensions; convert, by employing the scale information, the relative dimensions to the absolute dimensions; and output three-dimensional information containing the absolute dimensions.

8 Claims, 14 Drawing Sheets

(51) Int. Cl.
    *G06T 17/00*         (2006.01)
    *G06V 10/24*         (2022.01)
    *H04N 23/67*         (2023.01)
    *H04N 23/50*         (2023.01)

(52) U.S. Cl.
    CPC ......... *H04N 23/672* (2023.01); *H04N 23/673* (2023.01); *G06T 2200/08* (2013.01); *G06T 2207/10068* (2013.01); *G06T 2207/10148* (2013.01); *H04N 23/555* (2023.01)

(56) References Cited

U.S. PATENT DOCUMENTS

| | | | |
|---|---|---|---|
| 2017/0238807 A9* | 8/2017 | Vertikov | A61B 5/1079 |
| 2017/0366773 A1* | 12/2017 | Kiraly | A61B 1/00006 |
| 2019/0204069 A1 | 7/2019 | Tatsuta et al. | |
| 2019/0231220 A1* | 8/2019 | Refai | A61B 1/00172 |
| 2020/0051261 A1 | 2/2020 | Tsuruyama et al. | |
| 2022/0051472 A1* | 2/2022 | Takahashi | G02B 23/24 |
| 2022/0385874 A1* | 12/2022 | Sakamoto | H04N 13/156 |
| 2023/0157526 A1* | 5/2023 | Jang | A61B 1/00045 |
| | | | 600/111 |

FOREIGN PATENT DOCUMENTS

| | | |
|---|---|---|
| JP | 5593004 B2 | 9/2014 |
| JP | 2020-024563 A | 2/2020 |
| JP | 2020-124541 A | 8/2020 |

* cited by examiner

IMAGE PROCESSING APPARATUS FOR A PLURALITY OF TIMESERIES IMAGES ACQUIRED BY AN ENDOSCOPE, IMAGE PROCESSING METHOD, AND RECORDING MEDIUM

TECHNICAL FIELD

The present invention relates to an image processing apparatus, an image processing method, and a recording medium.

BACKGROUND ART

In the related art, there is a known endoscope having a function for measuring the dimensions of an imaging subject (for example, see Patent Literature 1). In endoscopic examination or endoscopic treatment, it is recommended to change the procedures of polypectomy, Endoscopic Mucosal Resection (EMR)/Endoscopic Submucosal Dissection (ESD), etc. in accordance with the dimensions of a polyp, and dimensional measurement is effective in making decisions about the procedures. As a means for measuring the dimensions, for example, a stereo optical system or laser light is used. In Patent Literature 1, laser light is radiated onto an imaging subject, and markers for measuring the dimensions of the imaging subject are generated and displayed on the basis of an imaging-subject image in which spots of the laser light are formed.

Meanwhile, in recent years, there have been advances in the development of technologies for generating three-dimensional information of an imaging subject from an image acquired by using a monocular optical system (for example, see Non-Patent Literature 1).

CITATION LIST

Patent Literature

{PTL 1} Japanese Unexamined Patent Application, Publication No. 2020-124541

Non-Patent Literature

{NPL 1} ZHOU, Tinghui et. al, "Unsupervised Learning of Depth and Ego-Motion from Video", 2017 IEEE Conference on Computer Vision and Pattern Recognition

SUMMARY OF INVENTION

Technical Problem

In the case of Patent Literature 1, it is necessary to provide the endoscope with a laser module that radiates the laser light for taking measurements. Accordingly, in order to measure the dimensions of the imaging subject, special equipment, such as a stereo optical system or a laser module, is required, and thus, it is not possible to measure the dimensions of an imaging subject by using a general monocular endoscope used in normal examination or treatment.

Three-dimensional reconstruction performed by using a monocular endoscope, as disclosed in Non-Patent Literature 1, is merely the reconstruction of a relative three-dimensional shape, and thus, it is not possible to acquire the absolute dimensions of an imaging subject.

In three-dimensional reconstruction, it is possible to estimate the dimensions of an imaging subject by capturing an object having known dimensions, such as a scale, together with the imaging subject and by comparing the size of the object and the imaging subject. However, in this case, special work for causing the object to be captured in the image is required. In addition, in the case of an endoscope with which the interior of a living body is observed, it is difficult to dispose an object having known dimensions at an imaging subject.

The present invention has been conceived in light of the above-described circumstances, and an object thereof is to provide an image processing apparatus, an image processing method, and a non-transitory recording medium with which it is possible to measure absolute dimensions of an imaging subject from an image acquired by a general monocular endoscope.

Solution to Problem

An aspect of the present invention is an image processing apparatus to which a plurality of time-series images acquired by an endoscope are input together with focus information of each of the plurality of images, the image processing apparatus comprising a processor, wherein the processor is configured to: reconstruct, by employing the plurality of images, three-dimensional information of an imaging subject containing relative dimensions, calculate, on the basis of the focus information, scale information for converting the relative dimensions of the three-dimensional information to absolute dimensions, convert, by employing the scale information, the relative dimensions to the absolute dimensions, and output three-dimensional information containing the absolute dimensions.

Another aspect of the present invention is an image processing method including: reconstructing, by employing a plurality of time-series images acquired by an endoscope, three-dimensional information of an imaging subject containing relative dimensions; calculating, on the basis of focus information of each of the plurality of images, scale information for converting the relative dimensions of the three-dimensional information to absolute dimensions; converting, by employing the scale information, the relative dimensions to the absolute dimensions; and outputting three-dimensional information containing the absolute dimensions.

Another aspect of the present invention is a computer-readable non-transitory recording medium that stores an image processing program, wherein the image processing program causes a computer to execute: reconstructing, by employing a plurality of time-series images acquired by an endoscope, three-dimensional information of an imaging subject containing relative dimensions; calculating, on the basis of focus information of each of the plurality of images, scale information for converting the relative dimensions of the three-dimensional information to absolute dimensions; converting, by employing the scale information, the relative dimensions to the absolute dimensions; and outputting three-dimensional information containing the absolute dimensions.

DESCRIPTION OF EMBODIMENT

An image processing apparatus, an image processing method, and a recording medium according to an embodiment of the present invention will be described below with reference to the drawings.

Figure 1:
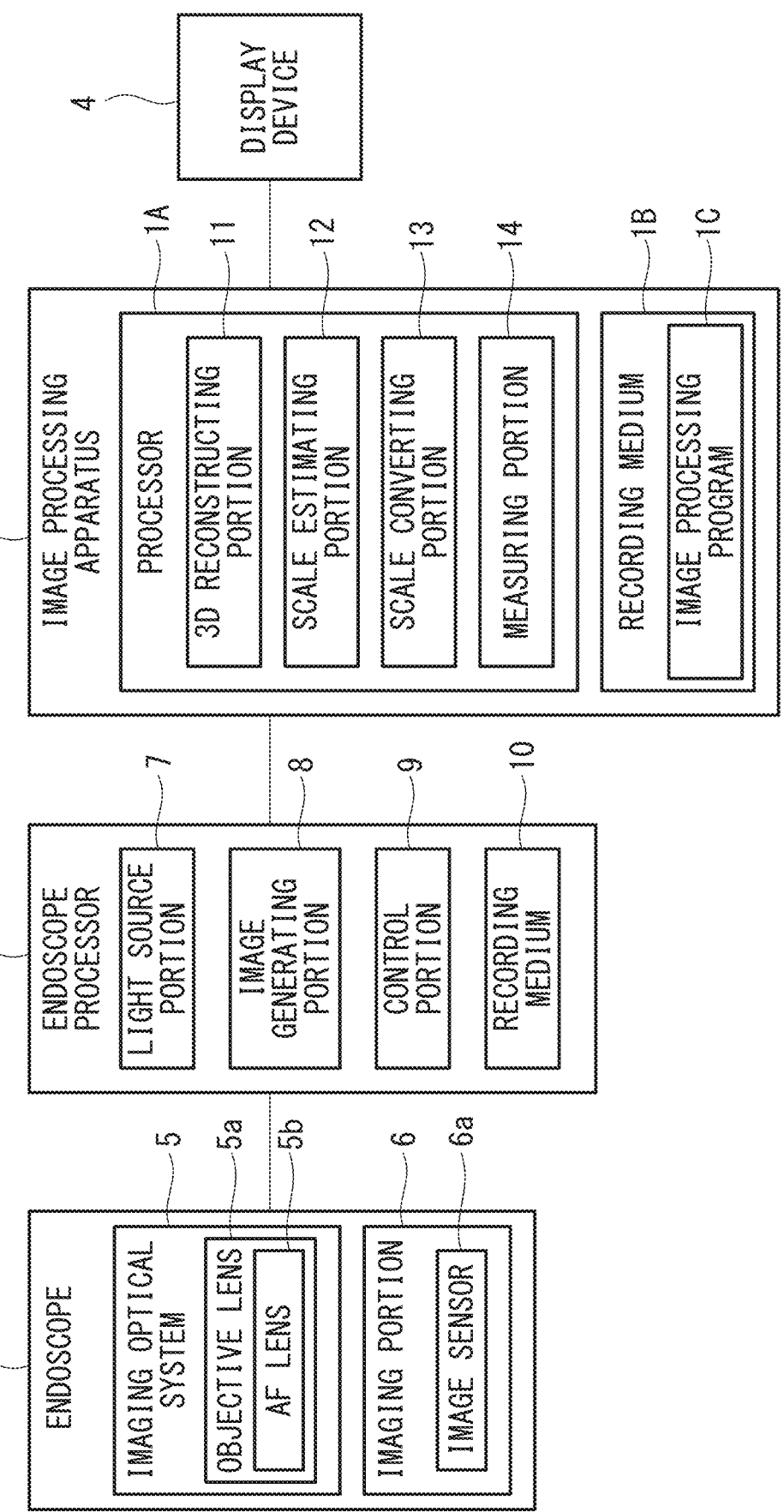
FIG. 1 is an overall configuration diagram of an endoscope system according to an embodiment of the present invention.

FIG. 1 shows an endoscope system 100 including an image processing apparatus 1 according to this embodiment. The endoscope system 100 includes an endoscope 2, an endoscope processor 3, the image processing apparatus 1, and a display device 4.

The endoscope 2 is a monocular endoscope that has an objective lens 5a. The endoscope 2 includes an imaging optical system 5 and an imaging portion 6.

The imaging optical system 5 has the objective lens 5a and an actuator (not shown), and the objective lens 5a has an autofocus (AF) lens 5b that can be moved along an optical axis thereof. The actuator moves the AF lens 5b in accordance with focus control information from the endoscope processor 3, and thereby the focal position of the objective lens 5a is automatically controlled.

The imaging portion 6 has an image sensor 6a. The image sensor 6a captures an optical image of an imaging subject formed by the objective lens 5a and generates image signals of the imaging subject.

The image sensor 6a may have a plurality of image-plane phase difference pixels that detect a phase difference. The phase difference corresponds to the amount of positional displacement that occurs between two imaging-subject images in an out-of-focus state in which the imaging subject is not in focus by the objective lens 5a. The image-plane phase difference pixels are at least some of the pixels arrayed on an imaging surface.

Figure 3A:
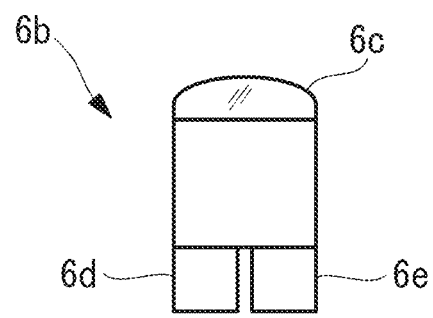
FIG. 3A is a diagram showing an example configuration of an image-plane phase difference pixel.
Figure 3B:
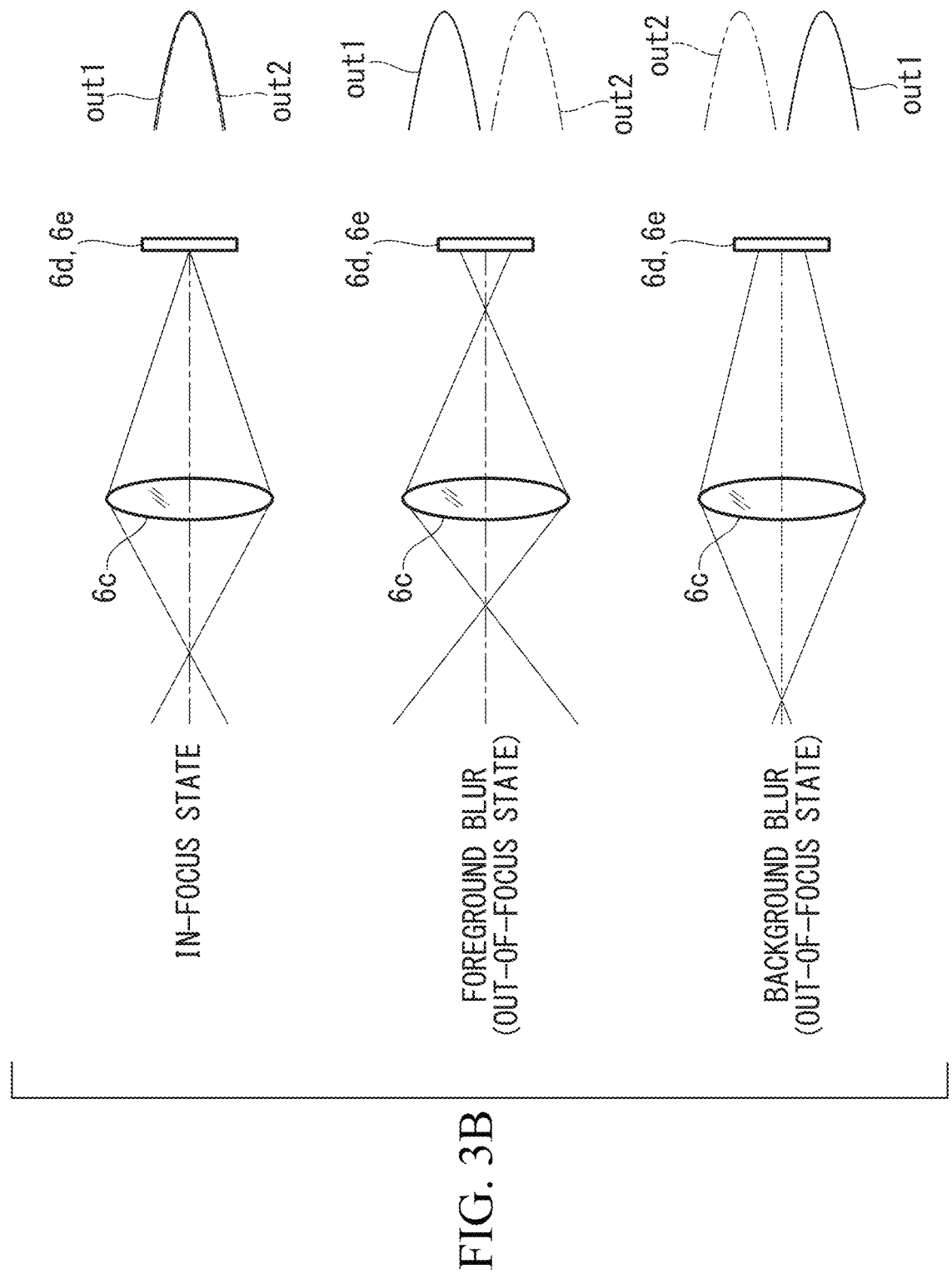
FIG. 3B is a diagram for explaining the relationship between the degree of focus and a pair of image-plane phase difference pixel outputs.

FIG. 3A shows an example configuration of the image-plane phase difference pixel. Each of the image-plane phase difference pixels has one microlens 6c and a pair of photoelectric converters 6d and 6e that convert light that has passed through the microlens 6c to electrical signals, and the pair of photoelectric converters 6d and 6e receive different luminous fluxes. FIG. 3B shows the relationship between the degree of focus and outputs, out1 and out2, of an image-plane phase difference pixel. In an in-focus state in which the imaging subject is in focus by the objective lens 5a, the two outputs, out1 and out2, of the photoelectric converters 6d and 6e coincide with each other. In the case of foreground blur or background blur, which is an out-of-focus state, the two outputs, out1 and out2, of the photoelectric converters 6d and 6e are different from each other. More specifically, in the case of foreground blur or background blur, the two outputs, out1 and out2, of the photoelectric converters 6d and 6e exhibit different aspects from each other. The phase difference is the amount of positional displacement between an image based on image signals obtained from the plurality of first photoelectric converters 6d and an image based on image signals obtained from the plurality of second photoelectric converters 6e.

Figure 4A:
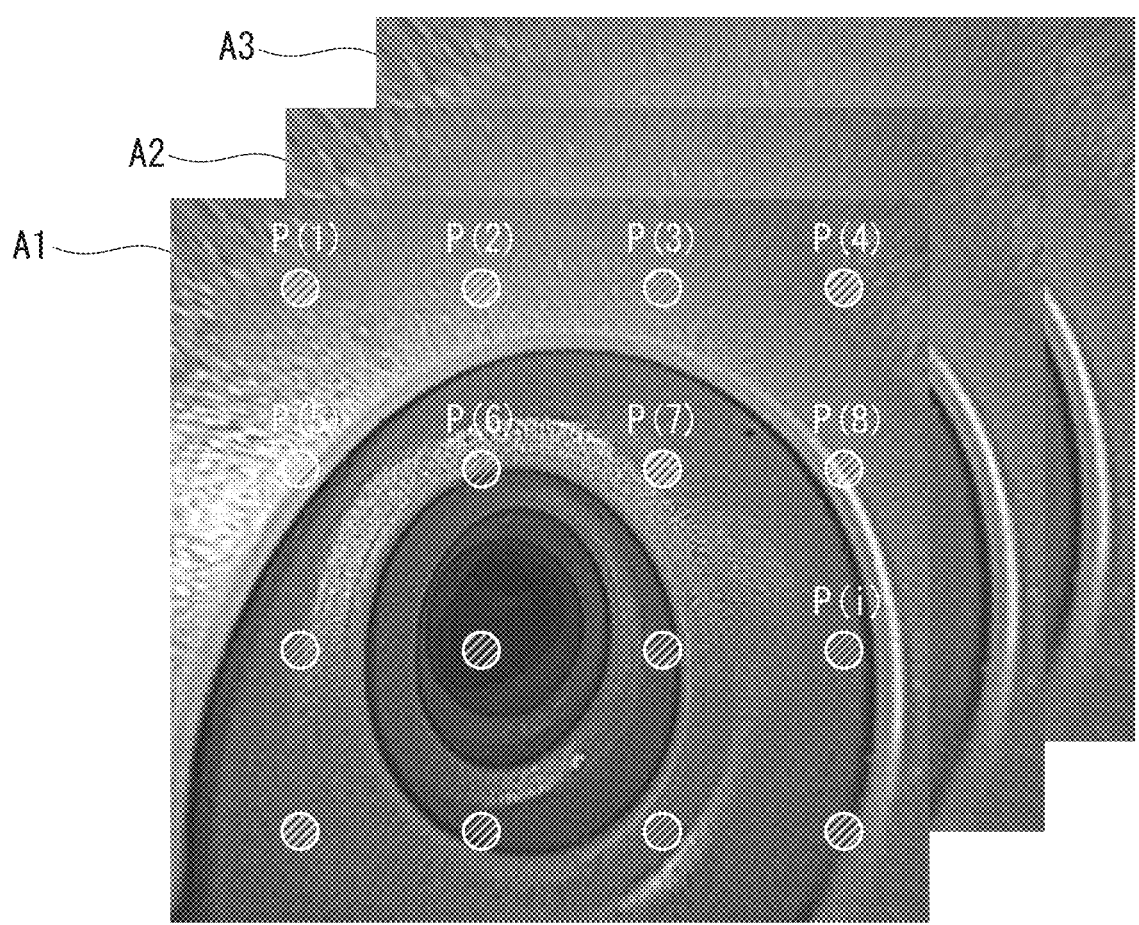
FIG. 4A is a diagram for explaining measurement regions in an image.

As shown in FIG. 4A, the imaging portion 6 has a plurality of measurement regions P(1), P(2), P(3) . . . . The imaging portion 6 calculates the degree of focus of each of the plurality of measurement regions P(1), P(2), P(3) . . . and outputs the degrees of focus to the endoscope processor 3 together with the image signals. Note that the plurality of measurement regions P(1), P(2), P(3) . . . are set in each of images A1, A2, A3 . . . and represented by small regions or points.

In the case in which the image sensor 6a does not have the image-plane phase difference pixels, the focal point of the objective lens 5a is automatically controlled by means of a contrast method. In this case, the degree of focus is the contrast of the image signals. The contrast is highest in the in-focus state and decreases with an increase in the displacement of the focal point from the imaging subject.

In the case in which the image sensor 6a has the image-plane phase difference pixels, the focal point of the objective lens 5a is automatically controlled by means of an image-plane phase difference method. In this case, the degree of focus is the phase difference detected by the image-plane phase difference pixels. The phase difference is zero in the in-focus state and increases with an increase in the displacement of the focal point from the imaging subject.

The endoscope processor 3 includes a light source portion 7, an image generating portion 8, a control portion 9, and a recording medium 10.

The light source portion 7 has a light source that emits illumination light for illuminating the imaging subject and provides the endoscope 2 with the illumination light.

The image generating portion 8 generates two-dimensional images from the image signals input to the endoscope processor 3 from the imaging portion 6. The image generating portion 8 may apply, as needed, processing, such as color correction processing and gamma correction processing, to the images.

The control portion 9 has a processor and the recording medium 10 stores a control program for the control portion 9 to control the light source portion 7 and the imaging optical system 5.

The control portion 9 automatically controls the focal point of the objective lens 5a by means of the contrast method or the image-plane phase difference method. Specifically, in the case of the contrast method, the control portion 9 generates focus control information on the basis of the contrast and transmits the focus control information to the imaging optical system 5. In the case of the image-plane phase difference method, the control portion 9 generates focus control information on the basis of the phase difference and transmits the focus control information to the imaging optical system 5. For example, the focus control information contains pulse signals, and the actuator moves the AF lens 5b in a stepwise manner in response to the pulse signals. Accordingly, the AF lens 5b is automatically moved to a position at which the imaging subject is in focus.

The control portion 9 causes the images generated by the image generating portion 8 to be output to the image processing apparatus 1 from the endoscope processor 3 together with the focus information. Therefore, the plurality of time-series images A1, A2, A3 . . . are input to the image processing apparatus 1 together with the focus information for each of the plurality of images A1, A2, A3 . . . The focus information is that related to the distance between the objective lens 5a and the imaging subject and, specifically, contains the focus control information containing the position of the AF lens 5b and the degree of focus (in other words, the contrast or the phase difference).

The image processing apparatus 1 includes a processor 1A, such as a central processing unit, and a recording medium 1B.

The recording medium 1B is a computer-readable non-transitory recording medium and is, for example, a publicly known magnetic disk, optical disk, flash memory, or the like. The recording medium 1B stores an image processing program 1C for causing the processor 1A to execute the image processing method, described later.

By executing the image processing program 1C, the processor 1A generates, from the images A1, A2, A3 . . . , three-dimensional (3D) information of the imaging subject containing absolute dimensions and measures the imaging-subject dimensions.

The display device 4 displays two-dimensional images A1, A2, A3 . . . input thereto from the image processing apparatus 1. The display device 4 may additionally display other information such as the settings of the endoscope 2 or the like. The display device 4 may display the 3D information and may display information about dimensions of the imaging subject measured from the 3D information.

Next, the image processing apparatus 1 will be described in detail.

Figure 2:
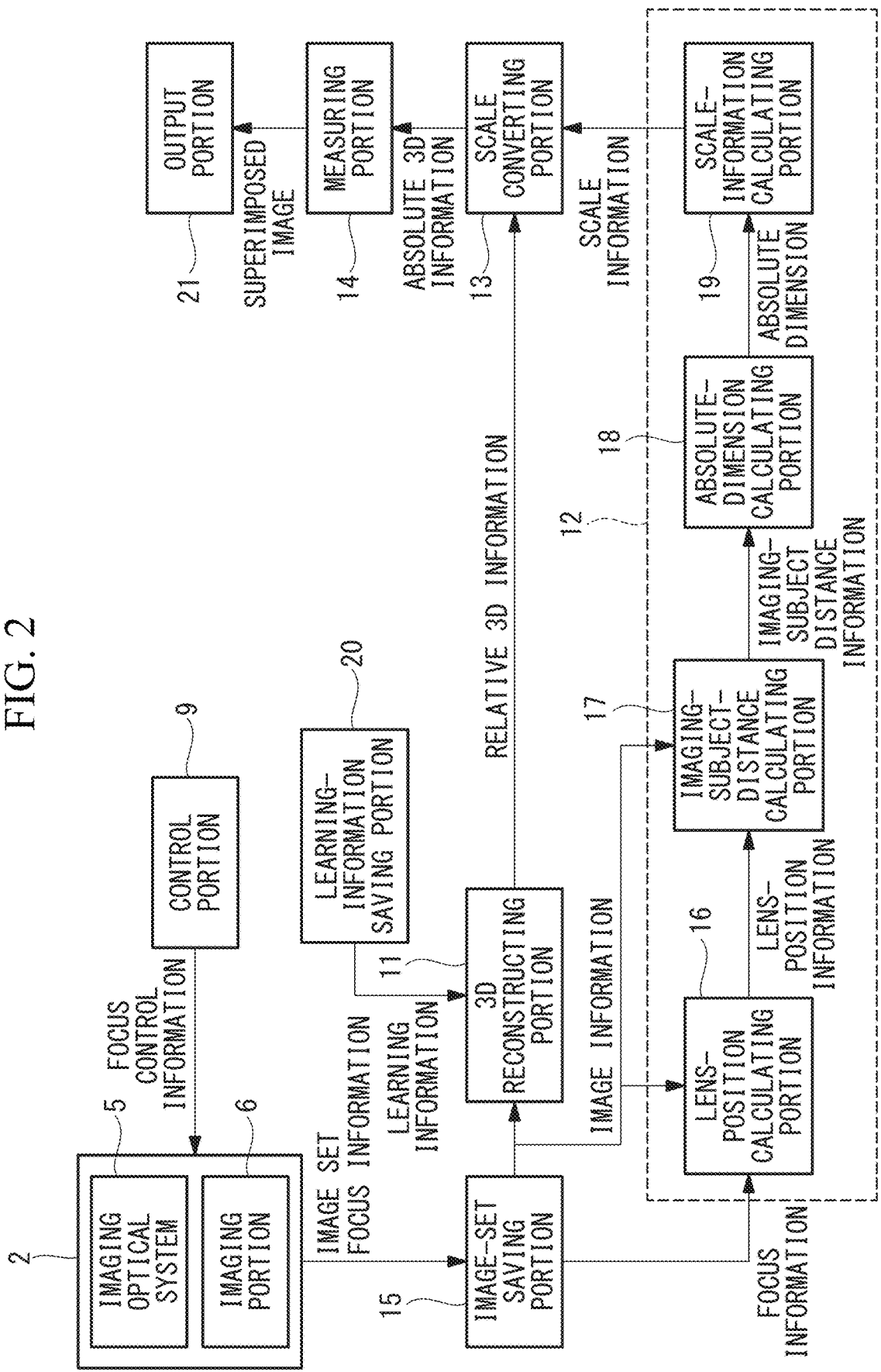
FIG. 2 is a functional block diagram of the endoscope system.

As shown in FIGS. 1 and 2, the image processing apparatus 1 has a three-dimensional (3D) reconstructing portion 11, a scale estimating portion 12, a scale converting portion 13, a measuring portion 14, and an image-set saving portion 15. The 3D reconstructing portion 11, the scale estimating portion 12, the scale converting portion 13, and the measuring portion 14 are realized as functions of the processor 1A.

The image-set saving portion 15 consists of an arbitrary memory. As described above, the plurality of time-series images A1, A2, A3 . . . are input to the image processing apparatus 1 from the endoscope processor 3. The image-set saving portion 15 at least temporarily saves an image set consisting of the images A1, A2, A3 . . . in association with the focus information of each of the images A1, A2, A3 . . . .

Figure 4B:
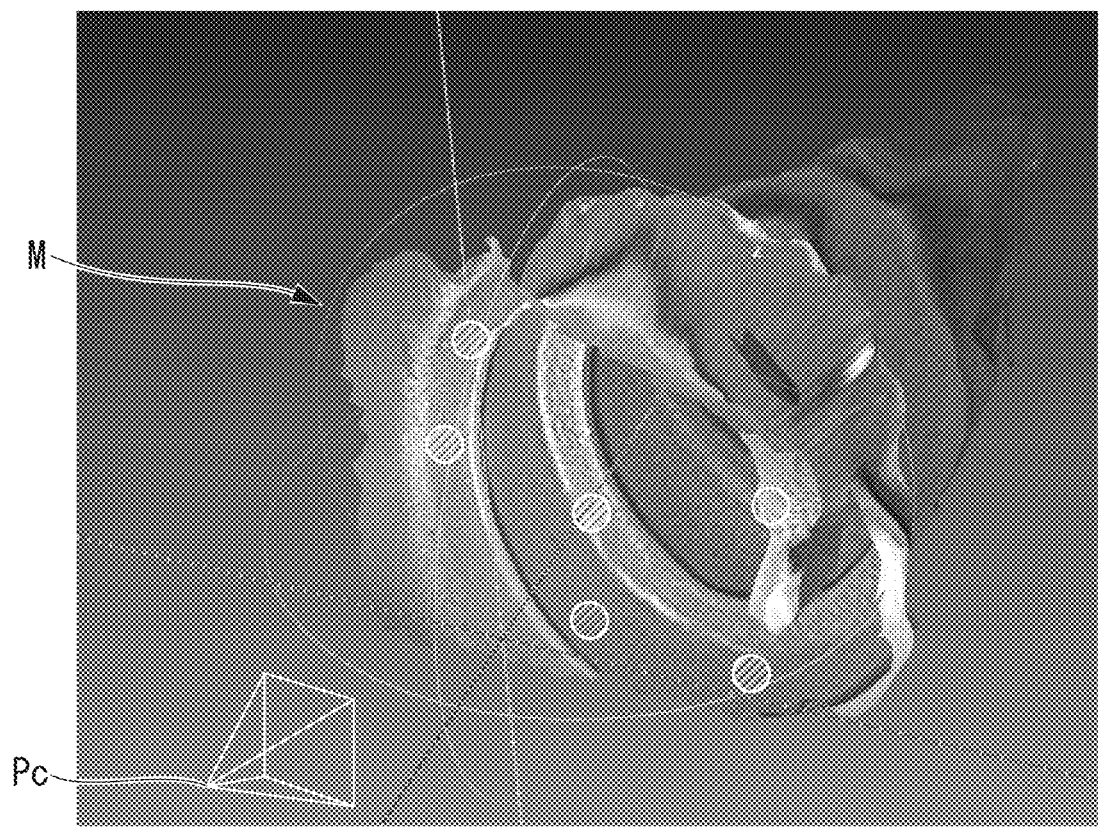
FIG. 4B is a diagram showing an example of relative three-dimensional information generated from an image set.

The 3D reconstructing portion 11 reads out the image set from the image-set saving portion 15 and generates 3D information M of the imaging subject from the image set. As shown in FIG. 4B, the 3D information M is a 3D model of the imaging subject and contains relative dimensions of the imaging subject. In the following, the 3D information containing the relative dimensions will also be referred to as the relative 3D information.

For example, the 3D reconstructing portion 11 estimates, by means of a Depth CNN (depth prediction convolutional neural network) and a Pose CNN (pose estimation convolutional neural network), depth information (depth map) in accordance with the image size, an extrinsic matrix and intrinsic parameters of a camera, and so forth, employs said information to compute 3D points corresponding to the respective pixels of the depth map, and thereby generates the relative 3D information M. In the case in which feature points of the imaging subject are utilized in the 3D reconstruction, the 3D reconstructing portion 11 may use learning information that is acquired by means of machine learning and that is saved in a learning-information saving portion 20 in advance.

The scale estimating portion 12 reads out the image set and the focus information from the image-set saving portion 15 and calculates scale information on the basis of the image set and the focus information. The scale information is that for converting the relative dimensions in the relative 3D information M to absolute dimensions.

Specifically, as shown in FIG. 2, the scale estimating portion 12 has a lens-position calculating portion 16, an imaging-subject-distance calculating portion 17, an absolute-dimension calculating portion 18, and a scale-information calculating portion 19.

As shown in FIG. 4A, the plurality of measurement regions P(1), P(2), P(3) . . . are set in all of the images A1, A2, A3 . . . used in the 3D information reconstruction. The respective measurement regions P(i) (i=1, 2 . . . , n) have the contrast or phase difference information, which is the degree of focus. The lens-position calculating portion 16 calculates, for the respective measurement regions P(i), the positions of the AF lens 5b at which the measurement regions P(i) are in focus on the basis of the focus control information and the degree of focus.

When a measurement region P(i) is in focus, the position of the AF lens 5b at which the measurement region P(i) is in focus is the same as the position of the AF lens 5b at the time of the image acquisition, the position being calculated from the focus control information. When a measurement region P(i) is not in focus, the position of the AF lens 5b at which the measurement region P(i) is in focus is displaced from the position of the AF lens 5b at the time of the image acquisition. The displacement amount of the AF lens 5b is calculated from the contrast or the phase difference.

Figure 5:
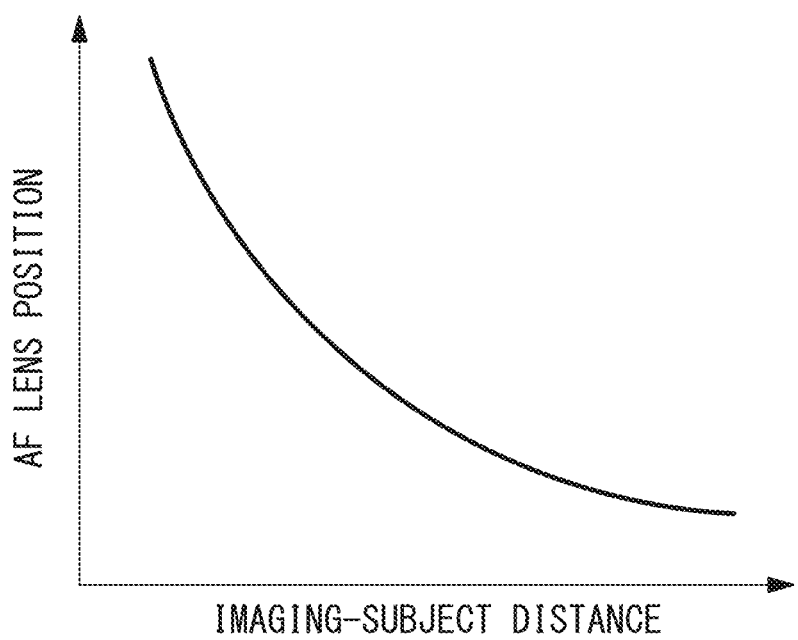
FIG. 5 is a diagram showing the correlation between the imaging-subject distance and the AF lens position in the in-focus state.

The imaging-subject-distance calculating portion 17 calculates an imaging-subject distance dt(i) for each of the plurality of measurement regions P(i) in each image Aj(j=1, 2, 3 . . . ) from the position of the AF lens 5b calculated by the lens-position calculating portion 16. The imaging-subject distance dt(i) is the actual distance (absolute distance) from the objective lens 5a to the imaging subject in the direction along the optical axis. As shown in FIG. 5, there is a prescribed correlation between the position of the AF lens 5b and the imaging-subject focus distance dt(i). The imaging-subject-distance calculating portion 17 calculates the imaging-subject distance dt(i) of each of the measurement regions P(i) on the basis of such a prescribed correlation.

The relative 3D information M contains the relative depth information (so-called depth map) for the respective positions in the imaging subject. Therefore, for each measurement region P(i), the imaging-subject distance dt(i), which is the absolute distance, and the relative distance corresponding to the imaging-subject distance dt(i) in the relative 3D information M are known. The absolute-dimension calculating portion 18 calculates, on the basis of the relative distances and the imaging-subject distances dt(i), absolute dimensions of regions corresponding to the respective measurement regions P(i) in the relative 3D information M.

Figure 6A:
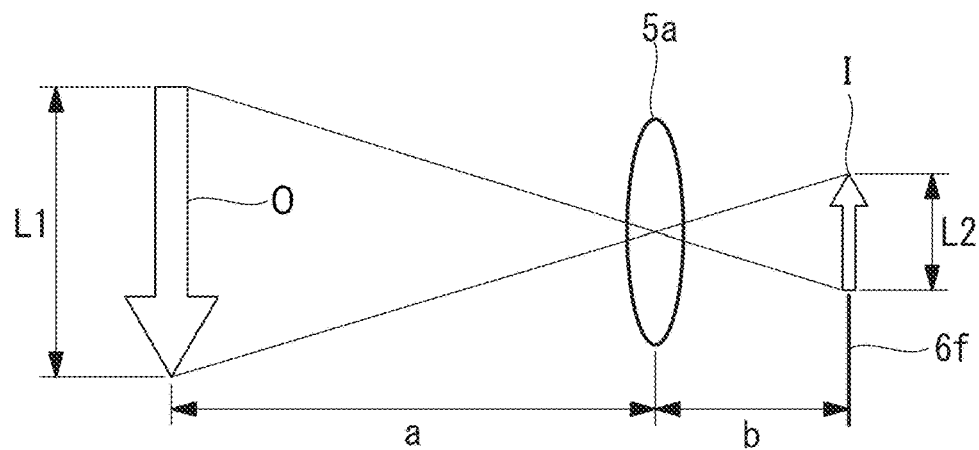
FIG. 6A is a diagram for explaining the geometric relationship between an object and an image in the in-focus state.
Figure 6B:
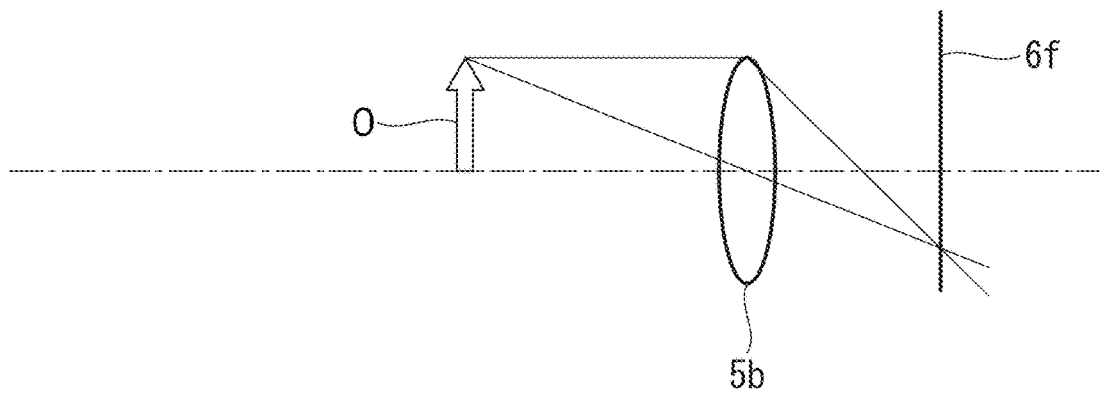
FIG. 6B is a diagram showing the AF lens position in the case in which the object distance is short.
Figure 6C:
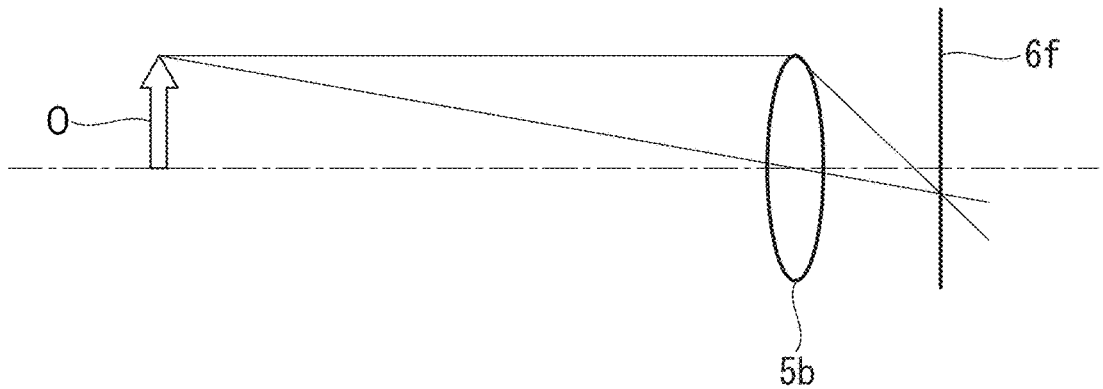
FIG. 6C is a diagram showing the AF lens position in the case in which the object distance is long.

FIGS. 6A to 6C explain a method for calculating the absolute dimensions of the imaging subject.

FIG. 6A shows the relationship between an object O, which is the imaging subject, and an image I of the object O, formed through the objective lens 5*a*. The object distance (imaging-subject distance) between the objective lens 5*a* and the object O is denoted by a, and the image distance between the objective lens 5*a* and an imaging surface 6*f* is denoted by b.

In order to form an image of the object O on the imaging surface 6*f* of the image sensor 6*a*, the AF lens 5*b* is moved in accordance with the object distance. Specifically, the AF lens 5*b* is moved toward the object O when the object distance a is short (see FIG. 6B) and is moved toward the image I when the object distance a is long (see FIG. 6C). In the in-focus state, the lens equation (a) holds. The focal distance of the objective lens 5*a* is denoted by f.

$$1/f = 1/a + 1/b \quad \text{(a)}$$

From equation (a) and equation (b) which represents an image-capturing magnification M, equation (c) is derived. L1 is the size of the object O and L2 is the size of the image I on the imaging surface 6*f*.

$$M = b/a = L2/L1 \quad \text{(b)}$$

$$M = f/(a-f) \quad \text{(c)}$$

Because the focal distance f is a design value of the objective lens 5*a*, the image-capturing magnification M is calculated from equation (c) as a result of acquiring the object distance a. The image-capturing magnification M may also be calculated from equation (b) as a result of acquiring the object distance a.

As shown in FIG. 5, in the in-focus state, there is a prescribed correlation between the object distance a and the position of the AF lens 5*b*. Therefore, the object distance a is calculated from the position of the AF lens 5*b* on the basis of this correlation. The correlation is stored, for example, in the recording medium 1B in the form of table data.

Next, the size L2 of the image I in an image is calculated from the number of pixels and the pixel size. The pixel size is the size of one pixel. Specifically, the size L2 is calculated by multiplying the number of pixels in the image I by the pixel size.

Next, the size L1 of the object O is calculated from equation (b) by employing the image-capturing magnification M and the size L2.

Figure 4C:
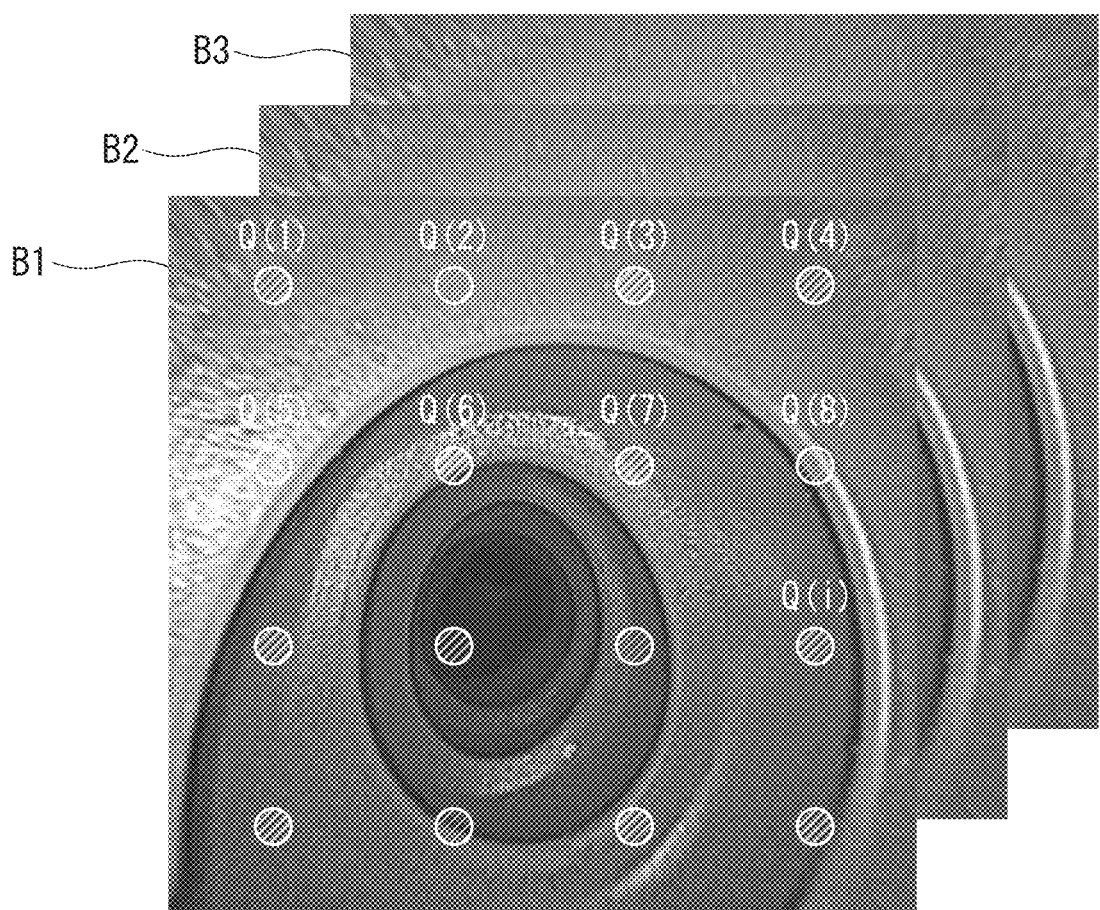
FIG. 4C is a diagram for explaining corresponding regions corresponding to the measurement regions.

As shown in FIG. 4C, the scale-information calculating portion 19 calculates relative distances ds(1), ds(2), ds(3) . . . of a plurality of corresponding regions Q(1), Q(2), Q(3) . . . that respectively correspond to the plurality of measurement regions P(1), P(2), P(3) . . . in the relative 3D information M. Specifically, a corresponding region Q(i) is a region in an image Bi corresponding to an image Aj viewed from the same point of view as the image Aj in the relative 3D information M. A relative distance ds(i) is a distance from a camera position Pc, which is the point of view, to a corresponding region Q(i) in the direction along the optical axis in the coordinate system of the relative 3D information M.

Next, the scale-information calculating portion 19 calculates scale information that minimizes the sum of differences between the imaging-subject distances dt(i) and the absolute distances converted from the relative distances ds(i) by employing the scale information. Specifically, the scale-information calculating portion 19 calculates, as the scale information, a coefficient $\alpha$ from equation (1) below.

$$a = \arg\min_{\beta} \sum_{i=0}^{n} (d_t(i) - \beta \cdot d_s(i)) \quad (1)$$

Here, n is the number of the measurement regions P(i) set in one image Aj and $\arg_\beta\min(f(\beta))$ is a function that returns a value of $\beta$ that minimizes $f(\beta)$.

The scale converting portion 13 employs the scale information to convert the relative dimensions of regions other than the measurement regions P(i) to the absolute dimensions. Specifically, as shown in equation (2) below, the scale converting portion 13 calculates the absolute dimensions dt of the other regions by multiplying the relative dimensions ds of the other regions by the coefficient $\alpha$.

$$dt = \alpha \times ds \quad (2)$$

As a result of the absolute dimensions of the measurement regions P(i) and the other regions being calculated in this way, 3D information containing the absolute dimensions of the imaging subject is generated. In the following, the 3D information containing the absolute dimensions will also be referred to as the absolute 3D information.

The measuring portion 14 executes, during the time when the measurement function of the image processing apparatus 1 is being executed, the measurement of the dimensions of the imaging subject in the absolute 3D information. The dimensions measured by the measuring portion 14 are the actual dimensions (absolute dimensions) of the imaging subject.

The measurement function may be executed on the basis of an instruction input to the image processing apparatus 1 or the endoscope processor 3 by a user. In this case, the measuring portion 14 may measure the length between a plurality of points. For example, the user can specify, by using an arbitrary input device, a plurality of points in the two-dimensional image or the 3D information displayed on the display device 4.

The measurement function may automatically be executed when a prescribed imaging subject is detected in the images A1, A2, A3 . . . . In this case, the measuring portion 14 may measure the dimensions of the prescribed imaging subject.

The measured dimension information of the imaging subject is superimposed on the two-dimensional images A1, A2, A3 . . . or the absolute 3D information to generate superimposed images, and the superimposed images are output to the display device 4 from an output portion 21. The absolute 3D information provided with scales representing the absolute dimensions may be output to the display device 4 from the output portion 21.

Next, the operation of the endoscope system 100 will be described.

Figure 7A:
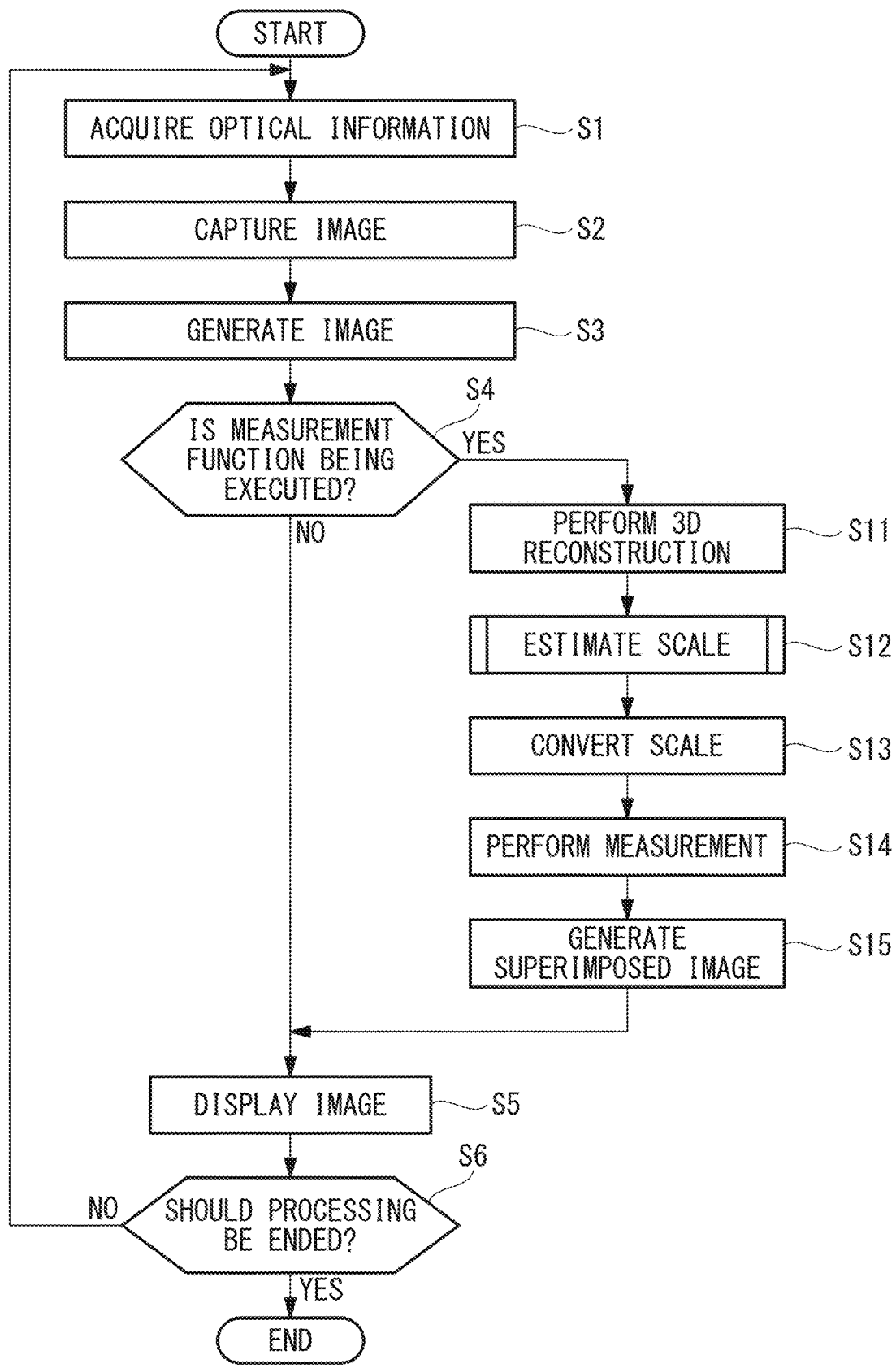
FIG. 7A is a flowchart of the operation of the endoscope system.

As shown in FIG. 7A, after turning on the endoscope system 100, optical information containing the focus control information is acquired (step S1), the imaging portion 6 captures images of an imaging subject (step S2), the image generating portion 8 generates images of the imaging subject (step S3), and the images are input to the image processing apparatus 1 together with the focus information.

Next, whether the measurement function is being executed is checked (step S4).

In the case in which the measurement function is not being executed ("NO" in step S4), the two-dimensional images generated in step S3 are transmitted to the display device 4 from the endoscope processor 3 via the image processing apparatus 1, and the two-dimensional images are displayed on the display device 4 (step S5).

In the case in which the measurement function is being executed ("YES" in step S4), the processing for measuring the absolute dimensions of the imaging subject is executed (steps S11 to S15). Steps S11 to S15 correspond to the image processing method executed by the image processing apparatus 1.

The image processing apparatus 1 temporarily saves the input images and the focus information in the image-set saving portion 15. After the image set required to generate the 3D information is accumulated in the image-set saving portion 15, the 3D reconstructing portion 11 reconstructs the relative 3D information M of the imaging subject by employing the image set (step S11).

Next, the scale estimating portion 12 calculates the scale information on the basis of the focus information and the image set (step S12).

Figure 7B:
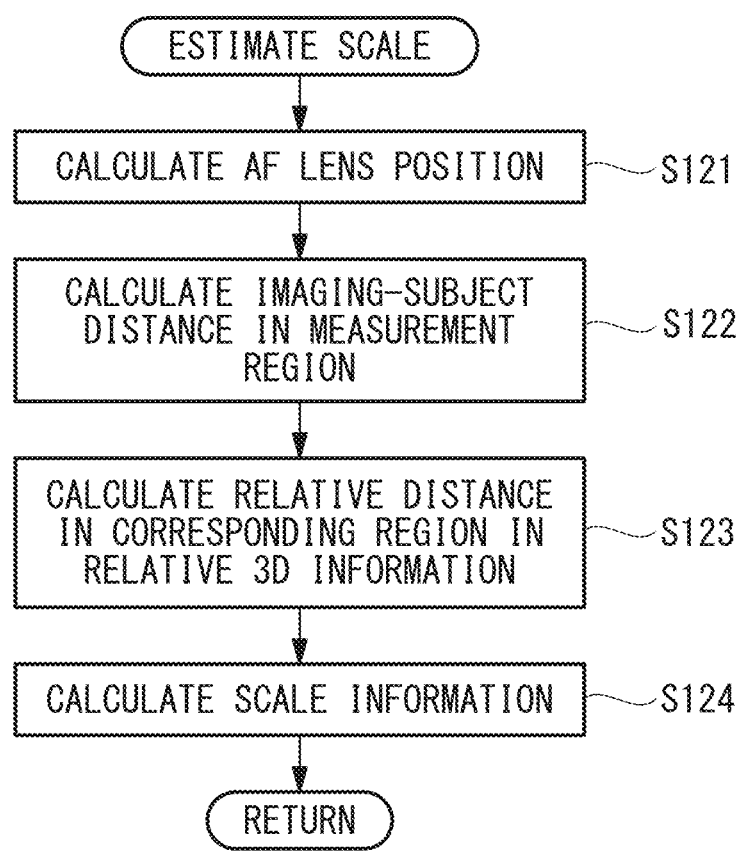
FIG. 7B is a flowchart of a scale estimation routine.

Specifically, as shown in FIG. 7B, the lens-position calculating portion 16 calculates, on the basis of the focus control information and the degree of focus, the position of the AF lens 5b for each of the plurality of measurement regions P(1), P(2), P(3) . . . in all of the images A1, A2, A3 . . . used to generate the relative 3D information M (step S121).

Next, the imaging-subject distances dt(i) of the respective measurement regions P(i) are calculated on the basis of the positions of the AF lens 5b (step S122), and the absolute dimensions of the respective measurement regions P(i) are calculated on the basis of the imaging-subject distances. Next, the relative distances ds(i) of the corresponding regions Q(i) corresponding to the measurement regions P(i) in the relative 3D information M are calculated (step S123), and the scale information is calculated on the basis of the imaging-subject distances dt(i) and the relative distances ds(i) (step S124). Specifically, the scale coefficient α is calculated from equation (1).

Next, the scale converting portion 13 converts the relative dimensions of the relative 3D information M to the absolute dimensions by employing the scale information (step S13). Specifically, the 3D information is enlarged or shrunk as a result of multiplying the relative dimensions of the respective positions in other regions in the relative 3D information M by the coefficient α, as indicated in equation (2), and thus, the absolute 3D information is generated.

Next, the measuring portion 14 measures the actual dimensions of the imaging subject in the absolute 3D information (step S14). Next, the measured dimension information is superimposed on the two-dimensional images or the 3D information to generate the superimposed images (step S15). The superimposed images are transmitted to the display device 4 from the output portion 21 and displayed on the display device 4 (step S5).

Steps S1 to S5 and S11 to S15 are repeated until an ending instruction is input to the endoscope system 100 (step S6).

As has been described, with this embodiment, the scale information for converting the relative dimensions of the relative 3D information M to the absolute dimensions is calculated by employing the focus information of the two-dimensional images. The focus information is that obtained from the general monocular endoscope 2 and the endoscope processor 3. Therefore, it is possible to measure the absolute dimensions of the imaging subject from the two-dimensional images acquired by means of the general monocular endoscope 2 without requiring special equipment or work.

In this embodiment, the endoscope 2 may have an EDOF (Extended Depth of Field) function for extending the depth of field and the image processing apparatus 1 may generate the 3D information from wide-focus images. The EDOF is a technology for obtaining a wide-focus image having an extended depth of field as compared with the depth of field of the objective lens 5a.

Figure 8:
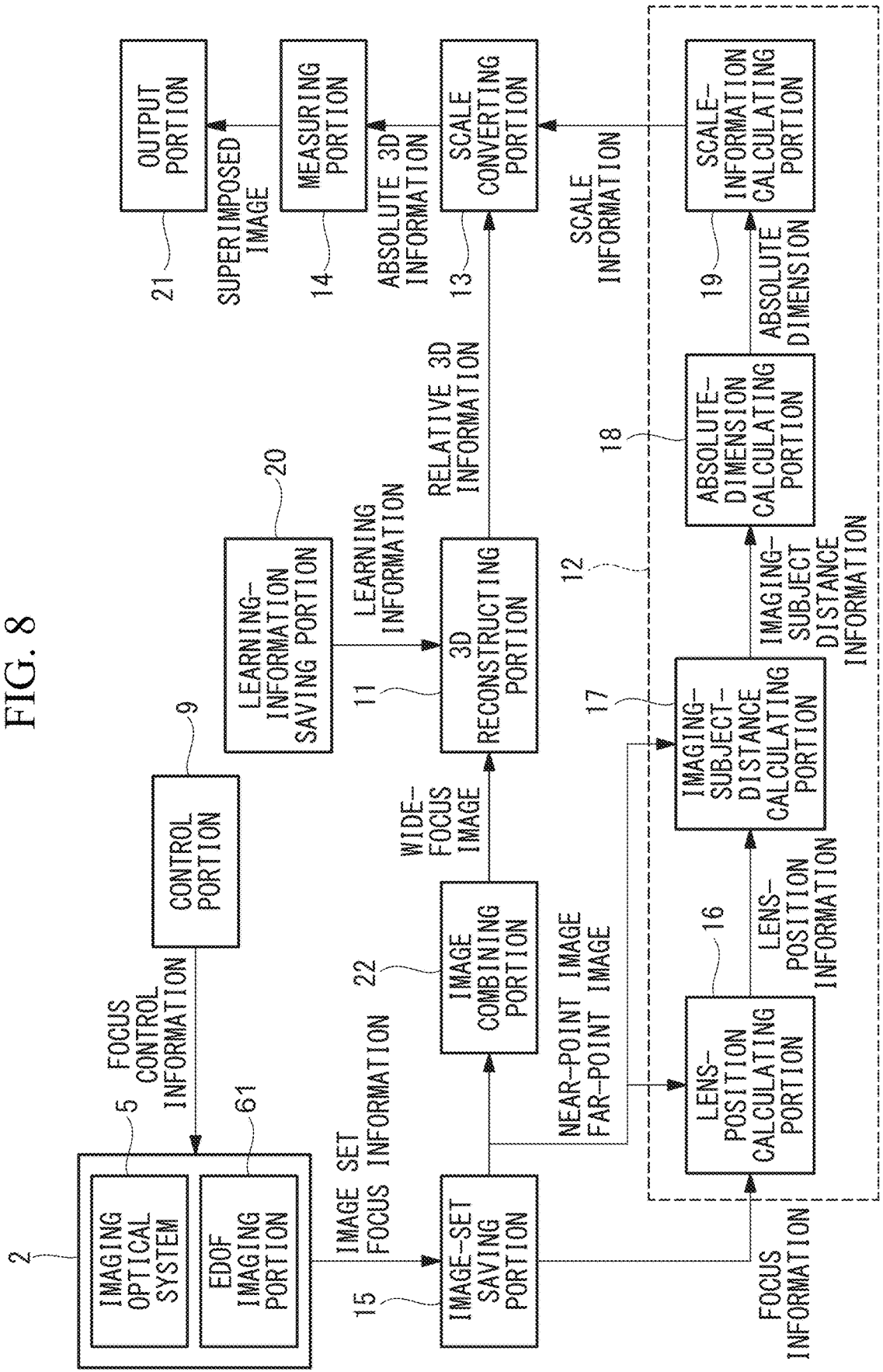
FIG. 8 is a functional block diagram of an endoscope system including an Extended Depth of Focus (EDOF) imaging portion.

FIG. 8 is a block diagram of the endoscope system 100 in which the endoscope 2 has an EDOF imaging portion 61 instead of the imaging portion 6. The EDOF imaging portion 61 simultaneously acquires, through an EDOF optical system, a plurality of image signals in which the focal positions are different in the optical axis direction.

Figure 9:
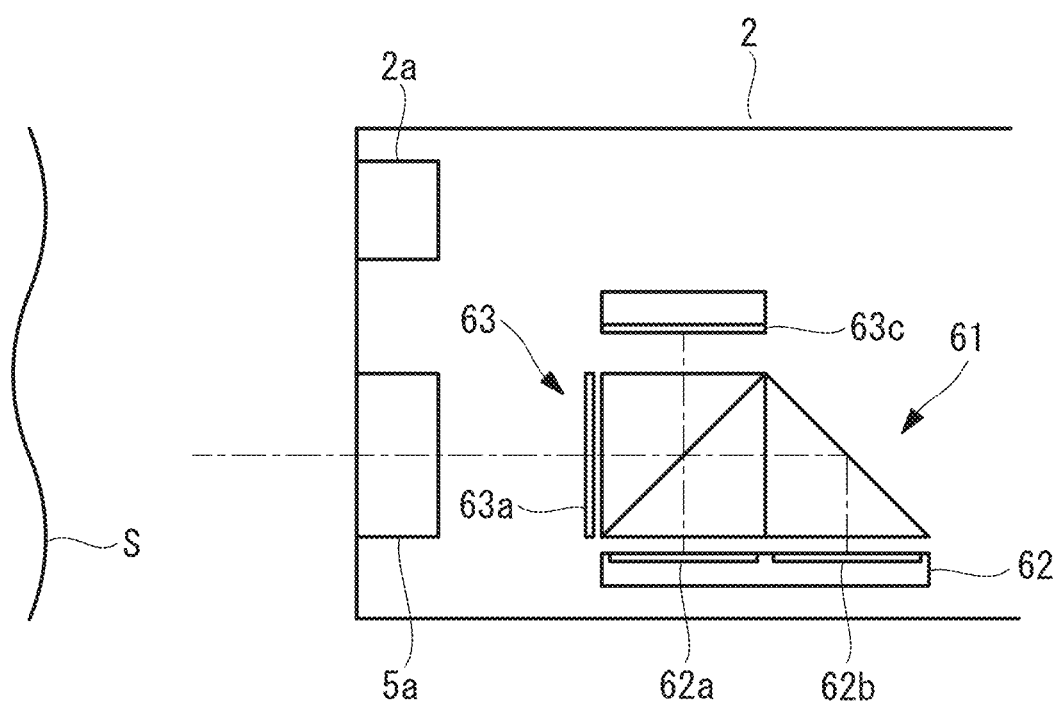
FIG. 9 is a diagram showing an example configuration of the EDOF imaging portion.

FIG. 9 shows a configuration of the EDOF imaging portion 61. Reference sign 2a is an illumination optical system that emits illumination light provided from the light source portion 7 toward the imaging subject. The EDOF imaging portion 61 has an image sensor 62 and an EDOF optical system 63. The EDOF optical system 63 has a ¼λ phase plate 63a and a beam splitter 63b and the image sensor 62 has two light reception regions 62a and 62b.

Light coming from an imaging subject S passes through the objective lens 5a and the ¼λ phase plate 63a and enters the beam splitter 63b. The beam splitter 63b splits the light coming from the imaging subject S into two light beams by polarization and creates an optical path difference between the two light beams. One of the light beams forms an image in the light reception region 62a and the other light beam forms an image in the light reception region 62b. The image sensor 62 simultaneously captures images of the two light reception regions 62a and 62b, and thereby generates near-point image signals in which a near point is in focus and far-point image signals in which a far point is in focus. Reference sign 63c is a mirror that reflects one of the light beams reflected by the beam splitter 63b toward the light reception region 62a.

The specific configuration of the EDOF imaging portion 61 is not limited to the above-described configuration and another configuration may be employed.

An image set consisting of a plurality of time-series pairs of the near-point images and the far-point images is input to the image processing apparatus 1 from the endoscope processor 3. The image-set saving portion 15 saves the near-point images and the far-point images respectively in association with the focus information.

The processor 1A additionally includes an image combining portion 22. The image combining portion 22 combines the near-point images and the far-point images to generate wide-focus images.

The 3D reconstructing portion 11 reconstructs the relative 3D information by employing the plurality of time-series wide-focus images.

Figure 10:
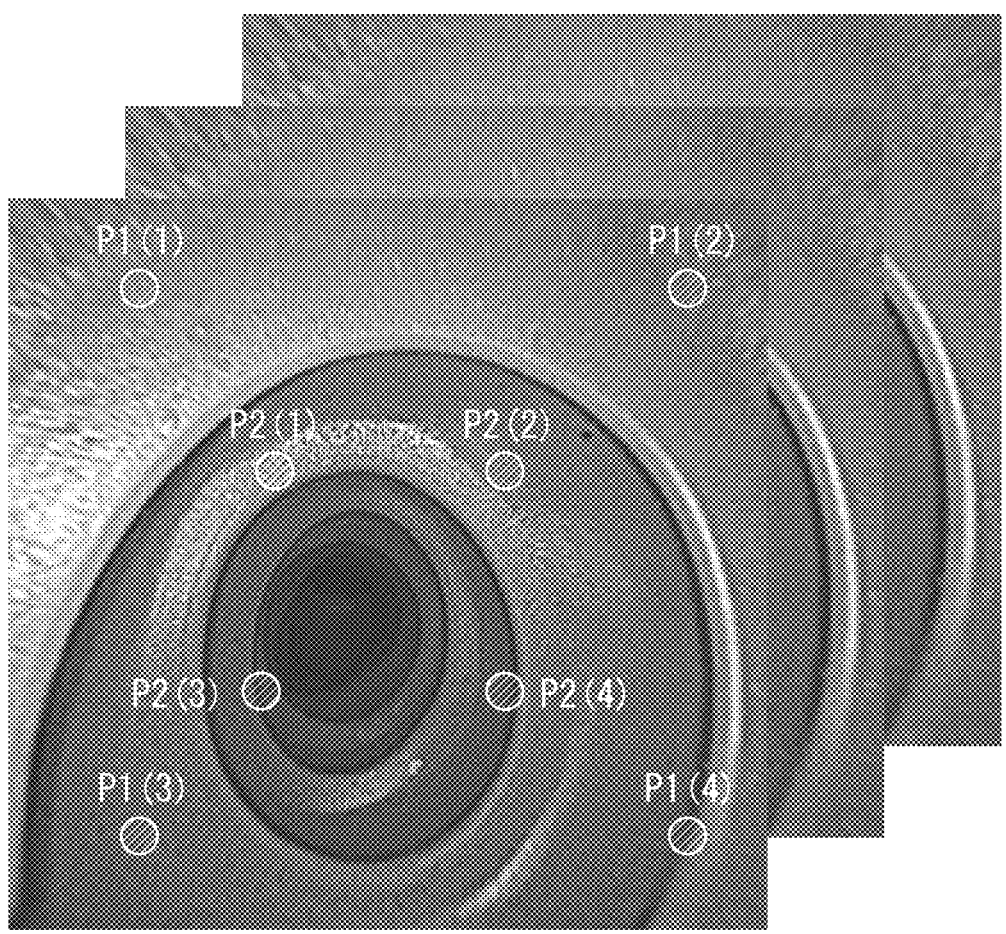
FIG. 10 is a diagram for explaining measurement regions in a near-point image and a far-point image.

As shown in FIG. 10, the plurality of measurement regions P1(1), P1(2) . . . are set in each of the near-point images and the plurality of measurement regions P2(1), P2(2) . . . are set in each of the far-point images. FIG. 10 shows the measurement regions P1($i$) and P2($i$) in the wide-focus images.

The lens-position calculating portion 16 calculates the positions of the AF lens 5b for the respective measurement regions P1($i$) and the imaging-subject-distance calculating portion 17 calculates the imaging-subject distances dt1($i$) of the respective measurement regions P1($i$). The scale-information calculating portion 19 calculates the relative distances ds1(*i*) of the corresponding regions corresponding to the measurement regions P1(*i*) and calculates the coefficient α1 from equation (1) by employing the distances dt1(*i*) and ds1(*i*).

Similarly, the lens-position calculating portion 16 calculates the positions of the AF lens 5*b* for the respective measurement regions P2(*i*) and the imaging-subject-distance calculating portion 17 calculates the imaging-subject distances dt2(*i*) of the respective measurement regions P2(*i*). The scale-information calculating portion 19 calculates the relative distances ds2(*i*) of the corresponding regions corresponding to the measurement regions P2(*i*) and calculates the coefficient α2 from equation (1) by employing the distances dt2(*i*) and ds2(*i*).

Therefore, two coefficients, α1 and α2 for the near point and the far point are obtained, and the near-point coefficient α1 and the far-point coefficient α2 could be different from each other.

The scale-information calculating portion 19 complements the coefficients at other focal points on the basis of the two coefficients, α1 and α2 for the near point and the far point. Therefore, the coefficients, α1 and α2 are calculated for each imaging-subject distance.

The scale converting portion 13 converts the relative dimensions of the other regions by employing the coefficients for the corresponding imaging-subject distances.

As above, as a result of using the EDOF endoscope 2, the scale information α1 and α2 are obtained for each imaging-subject distance, and it is possible to more accurately calculate the scale coefficients for regions other than the measurement regions P1(*i*) and P2(*i*). Accordingly, it is possible to more accurately calculate the absolute dimensions of the imaging subject for the other regions.

In this embodiment, the objective lens 5*a* has the AF lens 5*b*; however, alternatively, it is permissible that the objective lens 5*a* does not have the AF lens 5*b*, and the focal distance of the objective lens 5*a* may be fixed.

In this case, the focus information contains the phase difference, and it is not necessary to calculate the position of the AF lens 5*b* on the basis of the focus control information. The imaging-subject-distance calculating portion 17 calculates the imaging-subject distances of the measurement regions P(i) from the focal distance of the objective lens 5*a* and the phase difference.

As above, the embodiment of the present invention has been described in detail with reference to the drawings; however, specific configurations are not limited to the above-described embodiment and design alterations or the like within a range that does not depart from the scope of the present invention are also encompassed. In addition, the constituent elements indicated in the above-described embodiment and modifications can be configured, as appropriate, in combination.

REFERENCE SIGNS LIST

1 image processing apparatus
1A processor
1B recording medium
1C image processing program
2 endoscope
5*a* objective lens
5*b* autofocus lens
6*a* image sensor
63 EDOF optical system
A1, A2, A3 . . . image
M 3D information
P(1), P(2) . . . measurement region
Q(1), Q(2) . . . corresponding region

The invention claimed is:

1. An image processing apparatus comprising
a processor comprising hardware, wherein the processor is configured to:
   reconstruct, by employing a plurality of time-series images acquired by an endoscope with focus information of each of the plurality of time-series images, three-dimensional information of an imaging subject containing relative dimensions,
   calculate, on the basis of the focus information, scale information for converting the relative dimensions of the three-dimensional information to absolute dimensions,
   convert, by employing the scale information, the relative dimensions to the absolute dimensions, and
   output three-dimensional information containing the absolute dimensions;
wherein calculating the scale information comprises:
   calculating imaging-subject distances of a plurality of the measurement regions in each of the images on the basis of the focus information,
   calculating relative distances, from a camera position, of a plurality of corresponding regions respectively corresponding to the plurality of measurement regions in the three-dimensional information containing the relative dimensions, and
   calculating the scale information that minimizes the sum of differences between the imaging-subject distances and absolute distances converted from the relative distances by employing the scale information.

2. The image processing apparatus according to claim 1, wherein the scale information is a coefficient α calculated from equation (1) below, $$a = \arg\min_{\beta} \sum_{i=0}^{n}(d_t(i) - \beta \cdot d_s(i)) \quad (1)$$

wherein the processor converts the relative dimensions to the absolute dimensions on the basis of the relationship $d_t = \alpha \times d_s$,
where
dt(i) indicates the imaging-subject distance of the measurement region,
ds(i) indicates the relative distance of the corresponding region,
n indicates the number of measurement regions in each of the images,
$\arg_\beta \min(f(\beta))$ indicates a function that returns the value of β that minimizes f(β),
ds is the relative dimensions of the three-dimensional information, and
dt is the absolute dimensions of the three-dimensional information.

3. The image processing apparatus according to claim 1, wherein:
the plurality of images are acquired by an image sensor through an objective lens and the objective lens has an autofocus lens;
the focus information contains contrast of the images; and calculating the scale information includes
   calculating the positions of the autofocus lens on the basis of the contrast of the images,
   calculating the image-subject distances on the basis of the positions of the autofocus lens, and
   calculating the scale information on the basis of the imaging-subject distances.

4. The image processing apparatus according to claim 1, wherein:
   the plurality of images are acquired by an image sensor through an objective lens, the objective lens has an autofocus lens, and the image sensor has phase difference pixels;
   the focus information contains the phase difference detected by the phase difference pixels; and
   calculating the scale information includes
      calculating the positions of the autofocus lens on the basis of the phase difference,
      calculating the imaging-subject distances on the basis of the positions of the autofocus lens, and
      calculating the scale information on the basis of the imaging-subject distances.

5. The image processing apparatus according to claim 1, wherein:
   the plurality of images are acquired by an image sensor through an objective lens, the objective lens has a fixed focal distance, and the image sensor has phase difference pixels;
   the focus information is phase difference detected by the phase difference pixels; and
   calculating the scale information includes
      calculating the imaging-subject distances on the basis of the phase difference and the focal distance, and
      calculating the scale information on the basis of the imaging-subject distances.

6. The image processing apparatus according to claim 1, wherein:
   the plurality of images are multiple sets of images, each set consisting of at least two images that are simultaneously captured through an extended depth of focus optical system and in which focal positions thereof are different from each other in the optical axis direction; and
   the processor is configured to calculate the scale information by employing the at least two images.

7. An image processing method comprising:
   reconstructing, by employing a plurality of time-series images acquired by an endoscope, three-dimensional information of an imaging subject containing relative dimensions;
   calculating, on the basis of focus information of each of the plurality of images, scale information for converting the relative dimensions of the three-dimensional information to absolute dimensions;
   converting, by employing the scale information, the relative dimensions to the absolute dimensions; and
   outputting three-dimensional information containing the absolute dimensions;
   wherein calculating the scale information comprises:
      calculating imaging-subject distances of a plurality of the measurement regions in each of the images on the basis of the focus information,
      calculating relative distances, from a camera position, of a plurality of corresponding regions respectively corresponding to the plurality of measurement regions in the three-dimensional information containing the relative dimensions, and
   calculating the scale information that minimizes the sum of differences between the imaging-subject distances and absolute distances converted from the relative distances by employing the scale information.

8. A computer-readable non-transitory recording medium that stores an image processing program, wherein
   the image processing program causes a computer to execute:
   reconstructing, by employing a plurality of time-series images acquired by an endoscope, three-dimensional information of an imaging subject containing relative dimensions;
   calculating, on the basis of focus information of each of the plurality of images, scale information for converting the relative dimensions of the three-dimensional information to absolute dimensions;
   converting, by employing the scale information, the relative dimensions to the absolute dimensions; and
   outputting three-dimensional information containing the absolute dimensions;
   wherein calculating the scale information comprises:
      calculating imaging-subject distances of a plurality of the measurement regions in each of the images on the basis of the focus information,
      calculating relative distances, from a camera position, of a plurality of corresponding regions respectively corresponding to the plurality of measurement regions in the three-dimensional information containing the relative dimensions, and
   calculating the scale information that minimizes the sum of differences between the imaging-subject distances and absolute distances converted from the relative distances by employing the scale information.

* * * * *